US008242287B2

(12) United States Patent
Schertzer et al.

(10) Patent No.: US 8,242,287 B2
(45) Date of Patent: Aug. 14, 2012

(54) PROCESS FOR REACTING AN α, β-UNSATURATED DICARBOXYLIC ACID COMPOUND WITH AN ETHYLENICALLY UNSATURATED HYDROCARBON

(75) Inventors: Bryan M. Schertzer, Geneva, IL (US); Timothy P. McGinnis, Wheaton, IL (US)

(73) Assignee: Nalco Company, Naperville, IL (US)

( * ) Notice: Subject to any disclaimer, the term of this patent is extended or adjusted under 35 U.S.C. 154(b) by 464 days.

(21) Appl. No.: 12/403,072

(22) Filed: Mar. 12, 2009

(65) Prior Publication Data
US 2010/0234621 A1    Sep. 16, 2010

(51) Int. Cl.
*C07D 307/34* (2006.01)
*C07D 307/36* (2006.01)
(52) U.S. Cl. ........................................ 549/255; 549/203
(58) Field of Classification Search .................. 549/255, 549/203
See application file for complete search history.

(56) References Cited

U.S. PATENT DOCUMENTS

| 3,172,892 A | 3/1965 | Le Suer et al. |
| 3,219,666 A | 11/1965 | Norman et al. |
| 3,272,746 A | 9/1966 | Le Suer et al. |
| 3,412,111 A | 11/1968 | Irwin et al. |
| 3,476,774 A | 11/1969 | Zaweski |
| 3,819,660 A | 6/1974 | Cahill et al. |
| 4,086,251 A | 4/1978 | Cengel et al. |
| 4,235,786 A | 11/1980 | Wisotsky |
| 4,736,044 A | 4/1988 | Hanson |
| 5,939,562 A | 8/1999 | Kapanen et al. |
| 2005/0081714 A1 | 4/2005 | Panchalingam et al. |

FOREIGN PATENT DOCUMENTS

EP    0 319 809 A2    11/1988

*Primary Examiner* — Taylor Victor Oh
(74) *Attorney, Agent, or Firm* — Benjamin E. Carlsen; Andrew D. Sorenson

(57) ABSTRACT

The invention provides an improved method of synthesizing chemicals according to the ene reaction. The method addresses two problems that previously could not be addressed simultaneously, preventing charring of the reaction, and preventing gaseous degradation of the reagents. The method involves adding a boron bearing compound and an aromatic/antioxidant compound to the ene reaction. Combining these two compounds together inhibits charring and also causes an effect that neither compound can accomplish alone. The addition of these two compounds together also more effectively prevents either of the reagents from degrading than when either reagent is added alone. As a result the method reduces costs by reducing the amount of reagents needed for a synthesis and further reduces costs by eliminating the need to filter out char from the end products of the ene reaction. The method is particularly useful in the ene reaction synthesis of ASA from olefins and maleic anhydride.

13 Claims, 1 Drawing Sheet

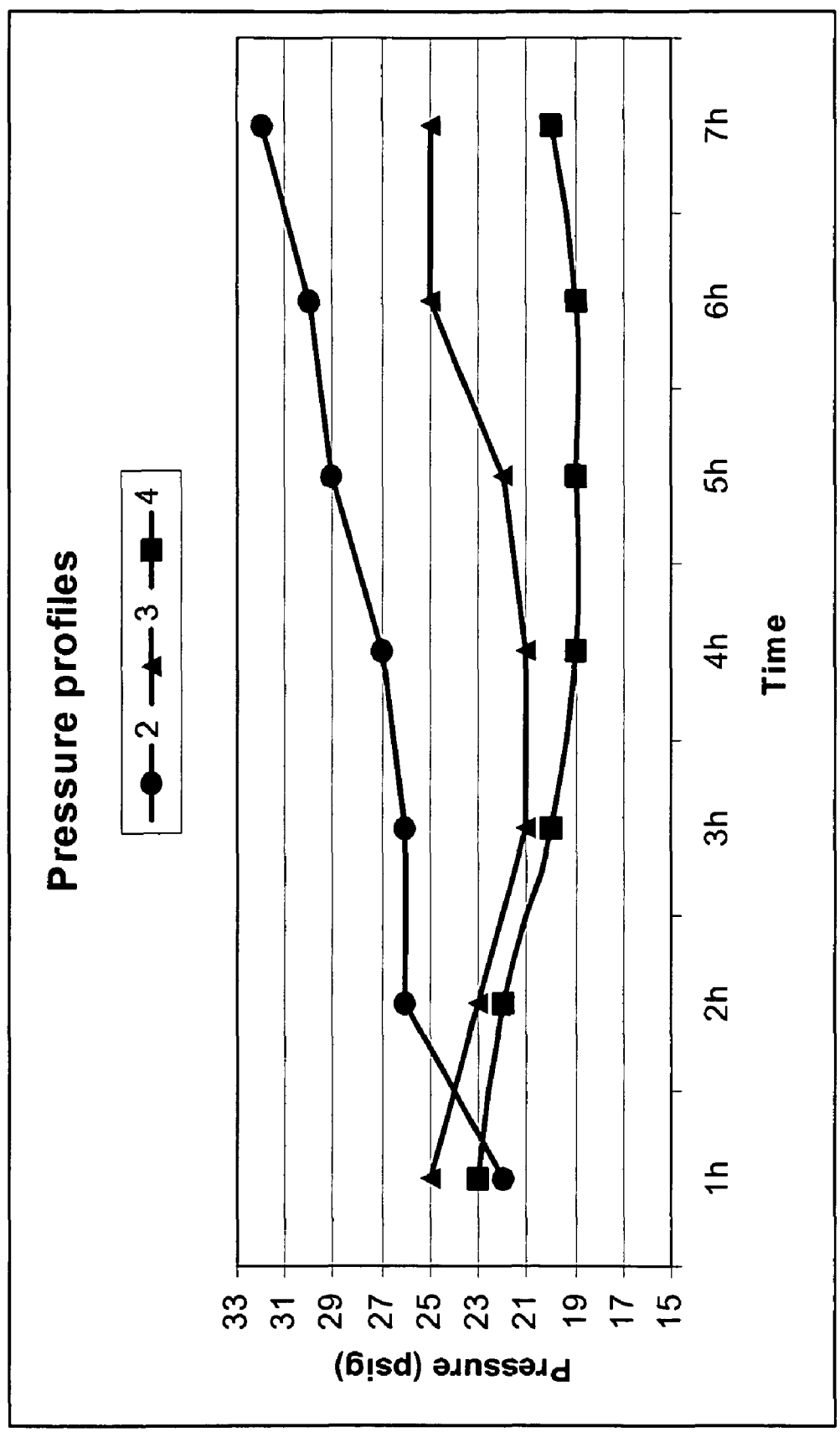

PROCESS FOR REACTING AN α, β-UNSATURATED DICARBOXYLIC ACID COMPOUND WITH AN ETHYLENICALLY UNSATURATED HYDROCARBON

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to compositions of matter and methods of using them to reduce charring of reagents in the "ene" reaction. In the ene reaction a molecule is formed by the reaction of an alkene reagent with an allylic hydrogen bearing reagent. The ene reaction is often facilitated by the use of extreme reaction conditions such as high temperatures and/or strong acids. One example of an ene reaction is the thermal reaction of reagents such as maleic anhydride and an olefin to form alkenyl succinic anhydride product. Details of how to perform an ene reaction are provided in U.S. Pat. Nos. 3,819,660, 3,219,666, 3,172,892, and 3,272,746.

Because of the extreme reaction conditions, ene reactions are often accompanied by an unwanted "charring". Charring is the degradation of some of the reagents into an insoluble, black, polymeric, solid, which resembles tar or charred material and is referred to as "char". This degradation is sometimes accompanied by the evolution of gaseous byproducts. The formation of char is problematic because it reduces the useful yield of the ene reaction, it causes discoloration of the products, and it requires the addition of a filtration step after the ene reaction to remove the char.

One previous attempt to prevent charring described in U.S. Pat. Nos. 4,736,044 and 4,086,251 involved adding boron or chlorine to the ene reaction. Another attempt described in U.S. Pat. No. 3,412,111 involved the addition of phenols to the ene reaction. A third attempt described in U.S. Pat. No. 3,476,774 involved the addition of anilines to the ene reaction. A fourth attempt described in U.S. Pat. No. 4,235,786 involved adding acid to the ene reaction. A fifth attempt described in European Patent EP 0 319 809 A2 involved adding a combination of butylated hydroxytoluene and oxalic acid to the ene reaction. The performance of these attempts however was unsatisfying because the additives reduced product yield by failing to inhibit charring completely and by partially degrading some of the reagents into gasses, leaving less raw material to produce the desired products.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists. All patents or patent applications mentioned anywhere in this application are hereby incorporated by reference in their entirety.

BRIEF SUMMARY OF THE INVENTION

At least one embodiment of the invention is directed towards a method for the chemical synthesis of products. The inventive method comprises reacting at least two reagents according to an ene reaction and adding to at least one of the reagents two compounds, one being a first compound and one being a second compound. The first compound is a boron bearing compound. The second compound is an aromatic or antioxidant-type compound. The first and second compounds are added in an amount effective in reducing char formation. The first and second compounds are added in an amount effective in reducing the degradation of at least one of the reagents into at least one gas by at least one of the compounds.

At least one embodiment of the invention is directed towards a method in which one of the reagents is an unsaturated α, β-dicarboxylic acid compound, one of the reagents is an unsaturated hydrocarbon, the boron bearing compound is boric oxide, and/or the aromatic/antioxidant compound is selected from the list consisting of: BHT, a hindered phenolic compound, and a hindered aniline compound. In addition, any one or combination of some, or all of these aromatic compounds can be added. The boron bearing compound can be added into the ene reaction at a level in excess of 50 ppm. An antioxidant can also be added to the ene reaction as can an acid.

At least one embodiment of the invention is directed towards a method in which the ratio of boron bearing compound to aromatic compound is within the range of 8:1 to 21:1, the boron bearing compound is added to a level of 100 ppm, and/or the aromatic compound is added to a level of 1800 ppm. In at least one embodiment of the invention the product of the chemical synthesis is ASA, one of the reagents is maleic acid, one of the reagents is an olefin, and/or one of the reagents is a 16-24 carbon olefin. The first and second compounds can be added in an amount effective in reducing the degradation of at least one of the reagents into at least one gas selected from the list consisting of: carbon dioxide, carbon monoxide, and ethyne.

BRIEF DESCRIPTION OF THE DRAWINGS

A detailed description of the invention is hereafter described with specific reference being made to the drawings in which:

FIG. 1 is a graph of pressure profiles of various reactions.

DETAILED DESCRIPTION OF THE INVENTION

For purposes of this application the definition of these terms is as follows:

"ASA" means alkenyl succinic anhydride.

"Antioxidant" means any agent, which slows or prevents oxidative damage or oxidation.

"Boron Bearing Compound" means a compound containing Boron.

"BHT" is butylated hydroxyltoluene.

"Char" means the resultants of those ene reaction reagents that rather than forming the desired product have instead degraded into an insoluble, black, polymeric, solid byproduct, which resembles tar or charred material.

"Charring" means the production of char.

"Ene reaction" means the addition of an enophile to an alkene through an allylic transposition and which is also known as "the Alder-ene reaction" and "ene synthesis".

"Oxygen-Boron Bearing Compound" means a compound containing an Oxygen atom which is both bonded to a Boron atom and is bonded to another atom including but not limited to boric acids, boric acid anhydrides, boric acid esters, and boron oxide salts.

In the event that the above definitions or a definition stated elsewhere in this application is inconsistent with a meaning (explicit or implicit) which is commonly used, in a dictionary, or stated in a source incorporated by reference into this application, the application and the claim terms in particular are understood to be construed according to the definition in this application, and not according to the common definition, dictionary definition, or the definition that was incorporated by reference.

In at least one embodiment an ene reaction is conducted in the presence of a boron bearing compound and also in the presence of an aromatic/antioxidant compound. The combination of these two agents in the ene reaction produces an unexpected synergistic effect especially at ratios other than 1:1. The combination of these two compounds completely inhibits the formation of char which has been shown to increase product yield. The product yield increases because each of the two compounds prevents the other reactants from performing a degrading side reaction that would otherwise reduce the amount of reagent available for conversion into product.

In at least one embodiment the ene reaction is between an unsaturated $\alpha,\beta$-dicarboxylic acid compound and an unsaturated hydrocarbon. In at least one embodiment the boron bearing compound is an oxygen-boron bearing compound. In at least one embodiment the boron bearing compound is boric oxide. In at least one embodiment, the aromatic compound is BHT, a hindered phenolc compound, or a hindered aniline compound. In at least on embodiment BHT, a hindered phenolic compound, a hindered aniline compound, or any combination thereof, are added to the ene reaction. In at least one embodiment the boron bearing compound is added into the ene reaction at a level in excess of 50 ppm. In at least one embodiment an antioxidant is also added to the ene reaction. In at least one embodiment an acid such as boric acid is also added to the ene reaction.

In at least one embodiment, the proportions of the boron bearing compound relative to the aromatic/antioxidant compound are such that they completely inhibit char formation. This proportion also reduces gaseous degradation of at least one of the reagents by either the boron bearing compound or the aromatic compound. One prior art method of using BHT together with boric acid as a char inhibitor for an ene reaction is described in U.S. Pat. No. 5,939,562. This prior art method however only utilized a 1:1 ratio of BHT with boric acid. A 1:1 ratio of the two has not been shown to be effective in producing the gaseous degradation reducing effect and completely inhibiting char. In at least one embodiment the ratio of boron bearing compound to aromatic/antioxidant compound is from between 8:1 to 21:1 by weight. U.S. Pat. No. 4,736,044 describes the use of other acids in reducing char but does not disclose completely inhibiting char.

By avoiding the reagent degradation effect, the ene reaction can be performed under different conditions than are commercially viable utilizing prior art methods. Prior art attempts at inhibiting charring involve running the ene reaction only for short lengths of time. This prevents both of the unwanted side effects (1-char formation and 2-gaseous degradation of reagents) from becoming too pronounced. By utilizing the aromatic/antioxidant compound and boron bearing compound in a proportion that displays the synergistic effect, both unwanted side effects can be avoided and the ene reaction can economically run for longer periods of time. Longer reaction times are more economical because they produce higher product yields.

In at least one embodiment, the reaction time is as long as 7 hours with no char. In at least one embodiment, the reaction time is as long as 10 hours with no char. In addition, the prior art discusses using a large excess of olefin reagent in the ene reaction to increase conversion and prevent charring. Such large excesses can often be as much as 50% to 100% of the molar amount of maleic anhydride in typical ene reactions. In at least one embodiment the reaction requires far less olefin, such as levels as low as 20%-5% of the molar amount of maleic anhydride to high conversion without the formation of char.

The following examples are presented to describe embodiments, utilities of the invention, and the unexpected synergistic effect. These examples are in no way meant to limit the invention unless otherwise stated in the claims.

TABLE 1

| Sample | O/MA | BHT | $B_2O_3$ | Time (hours) | Temp C. | MA | Olefin | Resulting Char** |
|---|---|---|---|---|---|---|---|---|
| 1 | 1.2:1 | 0.00% | 0.000% | 7 | 225 | 0.0% | 0.0% | 4* |
| 2 | 1.2:1 | 0.18% | 0.000% | 7 | 225 | 1.4% | 23.0% | 2 |
| 3 | 1.2:1 | 0.00% | 0.100% | 7 | 225 | 1.4% | 24.4% | 1 |
| 4 | 1.2:1 | 0.18% | 0.006% | 7 | 225 | 0.7% | 20.7% | 0 |

*Presumed based on Prior Art literature
**Scale for resulting char is:
0 - Completely Inhibited, No char visible in product and when the ene product is run through a 100 μm filter no char is deposited on the filter.
1 - Minimal Charring, No char visible in product, reactor is predominantly char free and when the ene product is run through a 100 μm filter small amounts of char are deposited on the filter.
2 - Significant Charring, No char visible in product, reactor is coated with a thin layer of char and when the ene product is run through a 100 μm filter the char clogs the filter.
3 - Much Charring, Some char is visible in product, reactor is coated with a thick layer of char and when the ene product is run through a 100 μm filter the char clogs the filter.
4 - Excessive Charring, Large amount of char is visible in product, reactor is coated with a thick layer of char, multiple filtration steps are required before the ene product can be run through a 100 μm filter.

Table 1 illustrates the results of four ASA producing thermal ene reactions involving reacting an 18 carbon olefin with maleic anhydride. A first control sample containing neither boric oxide nor BHT is presented based on the literature present in the Prior Art, which states that it would undergo excessive charring. In second sample BHT was added to the ene reaction at a level of 1800 ppm and significant charring was observed. In a third sample boric oxide was added to the ene reaction at a level of 100 ppm and minimal charring was observed. However, in the second and third samples in which only boric oxide or only BHT were added, significant increases in the vapor pressure of the reactions occurred due to large amounts of carbon dioxide being evolved. The carbon dioxide evolution was a result of the respective decomposing of the reaction components. Some of the byproduct may also have evolved as carbon monoxide and ethyne. As a result, while boric oxide alone or BHT alone did reduce charring, they also reduced yield of ASA because each decomposed some component needed to produce ASA.

In the fourth sample the ene reaction was performed with 100 ppm boric oxide along with 1800 ppm BHT. In that reaction, vapor pressure declined until the reaction reached a high level of conversion. The reduction in pressure indicated that maleic anhydride was not being degraded into carbon dioxide or other gasses and instead was being consumed as it produced ASA. As a result, a greater yield of ASA was realized.

FIG. 1 illustrates the pressure profiles of the samples presented in Table 1. FIG. 1 is a graph which shows that for the second and third prior art samples pressure rises more rapidly than in the fourth sample because they are undergoing decomposition into gasses. The fourth sample of the invention maintains low pressure up to the 7th hour indicating that product losing decomposition is not occurring.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. All patents and referenced materials mentioned herein are incorporated by reference in their entirety. Furthermore, the invention encompasses any possible combination of some or all of the various embodiments described herein and incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of synthesizing alkenyl succinic anhydride comprising:
reacting two reagents one of which is an olefin and one of which is a maleic anhydride, according to an ene reaction for at least 7 hours to form a product which comprises alkenyl succinic anhydride; and
adding a boron bearing compound and an aromatic/antioxidant compound to at least one of the reagents prior to the reaction, wherein:
the ratio of boron bearing compound to aromatic/antioxidant compound is within the range of 8:1 to 21:1 and thereby are in an amount effective in reducing char formation, and are in an amount effective in reducing the degradation of at least one of the reagents into a gas by at least one of the compounds,
the molar amount of olefin is no more than 20% of the molar amount of the maleic anhydride and no significant char results from the reaction and the yield of the alkenyl succinic anhydride is greater than a similar reaction in which the molar amount of olefin is at least more than 50% of the molar amount of the maleic anhydride and the ratio of boron bearing compound to aromatic/antioxidant compound is 1:1, and
the boron bearing compound and the aromatic/antioxidant compound are added in an amount effective in reducing the degradation of at least one of the reagents into at least one gas selected from the list consisting of: carbon dioxide, carbon monoxide, and ethyne.

2. The method of claim 1 wherein the olefin is an unsaturated $\alpha,\beta$-dicarboxylic acid compound.

3. The method of claim 1 wherein the boron bearing compound is boric oxide.

4. The method of claim 1 wherein the aromatic/antioxidant compound is selected from the list consisting of butylated hydroxytoluene, a phenolic compound which is sterically hindered so it inhibits the reaction, and an aniline compound which is sterically hindered so it inhibits the reaction.

5. The method of claim 1 wherein the boron bearing compound is added into the ene reaction at a level in excess of 50 ppm.

6. The method of claim 1 wherein an antioxidant is also added to the ene reaction.

7. The method of claim 1 wherein an acid is also added to the ene reaction.

8. The method of claim 1 wherein the boron bearing compound is added to a level of 100 ppm.

9. The method of claim 1 wherein the aromatic compound is added to a level of 1800 ppm.

10. The method of claim 1 wherein one of the reagents is maleic anhydride.

11. The method of claim 1 wherein one of the reagents is an 18-carbon olefin.

12. The method of claim 1 in which the boron bearing compound is an oxygen-boron bearing compound.

13. The method of claim 1 in which the char formation is reduced to such an extent that when the product of the ene reaction is passed through a 100 μm filter, no char is deposited on the filter.

* * * * *